United States Patent [19]

Durfor et al.

[11] Patent Number: 4,797,181

[45] Date of Patent: Jan. 10, 1989

[54] FLAVIN COFACTOR MODIFIED ELECTRODES AND METHODS OF SYNTHESIS AND USE

[75] Inventors: Charles N. Durfor, Rockville, Md.; Mark L. Bowers, Watertown; Barbara A. Yenser, Essex, both of Mass.

[73] Assignee: GTE Laboratories Incorporated, Waltham, Mass.

[21] Appl. No.: 81,251

[22] Filed: Aug. 3, 1987

[51] Int. Cl.$^4$ .......................................... B01D 59/40
[52] U.S. Cl. ................... 204/1 T; 204/403; 204/418; 435/291; 435/817
[58] Field of Search ................. 204/1 T, 290 R, 403, 204/418; 427/50, 77, 330, 414; 435/817, 291

[56] References Cited

U.S. PATENT DOCUMENTS

| | | | |
|---|---|---|---|
| 4,321,123 | 3/1982 | Nakamura et al. | 204/195 B |
| 4,357,142 | 11/1982 | Schall, Jr. et al. | 23/230 B |
| 4,414,080 | 11/1983 | Williams et al. | 204/129 |
| 4,439,302 | 3/1984 | Wrighton et al. | 204/290 R |
| 4,461,691 | 7/1984 | Frank | 204/242 |
| 4,490,464 | 12/1984 | Gorton et al. | 435/4 |
| 4,528,276 | 7/1985 | Matsunaga | 435/39 |
| 4,532,188 | 7/1985 | Naarmann et al. | 428/500 |
| 4,548,696 | 10/1985 | Wearer, Jr. | 204/290 R |
| 4,579,642 | 4/1986 | Niiyama et al. | 204/403 |
| 4,581,336 | 4/1986 | Malloy et al. | 435/176 |
| 4,582,805 | 4/1986 | Bozzelli et al. | 435/180 |
| 4,593,004 | 6/1986 | Boross et al. | 435/181 |
| 4,595,479 | 6/1986 | Kimura et al. | 204/294 |
| 4,609,600 | 9/1986 | Heinze et al. | 429/197 |
| 4,619,754 | 10/1986 | Niki et al. | 204/290 R |
| 4,657,873 | 4/1987 | Gadow et al. | 436/532 |
| 4,659,665 | 4/1987 | Freeman et al. | 435/182 |
| 4,679,562 | 7/1987 | Luksha | 128/635 |

OTHER PUBLICATIONS

Walker et al., *Eur. J. Biochem.*, 26, 279 (1972).
Frost et al., *J. Am. Chem. Soc.*, 102, 7157 (1980).
Wingard et al., "Flavins and Flavoproteins", p. 893, Walter de Gruyter & Co., Berlin & N.Y. (1984).
Miyawaki et al., *Biochimica et Biophysica Acta*, 838, 60 (1985).
Williams et al., *Biochem.*, 24, 7790 (1985).
Wingard et al., *Biotechnology and Bioengineering Symp.*, 8, 483 (1978).
Wingard, *Trends in Analytical Chemistry*, 3, 235 (1984).
Varfolomeyev et al., *J. Molecular Catalysis*, 27, 305 (1984).
Castner et al., *Biochemistry*, 23, 2203 (1984).
Wieck et al., *Analytica Chimica Acta*, 158, 137 (1984).
Wrighton, *Science*, 231, 32 (1986).
Bootsma et al., *J. Polymer Sci.: Polymer Chemistry Edn.*, 22, 705 (1984).
Foulds et al., *Bioessays*, 3, 129 (1985).
Bourdillon et al., *J. Electrochem. Soc.: Electrochemical Science and Technology*, 133, 706 (1986).

*Primary Examiner*—John F. Niebling
*Assistant Examiner*—Kathryn Gorgos
*Attorney, Agent, or Firm*—Frances P. Craig

[57] ABSTRACT

An electrochemically coupled cofactor modified electrode for mediating the heterogeneous or homogeneous catalysis of a biochemical reaction by an enzyme. The electrode coating comprises mercapto-flavin derivative bonded to the electrode surface. Methods for preparation and use of the modified electrode are also presented.

25 Claims, 1 Drawing Sheet

FLAVIN COFACTOR MODIFIED ELECTRODES AND METHODS OF SYNTHESIS AND USE

This invention was made as a result of work under Contract No. MDA-903-85-C-0031 awarded by the U.S. Department of the Navy. The Government has certain rights in this invention.

THE FIELD OF THE INVENTION

This invention relates to heterogeneous and homogeneous catalyses by immobilized or soluble enzymes in a biochemical reaction and, more particularly, to flavin cofactor modified electrodes and methods for electrochemically mediating such catalyses, as well as to methods for producing the cofactor modified electrode.

BACKGROUND OF THE INVENTION

In recent years, industrial applications for immobilized enzymes have grown dramatically, for example, in the diverse fields of fine pharmaceutical synthesis, clinical analysis, and in the production of bulk chemicals. However, the majority of industrial enzymes perform one of only three reactions: isomerization, hydrolysis or oxidation. None of these industrial enzymatic processes involves biological endothermic synthesis, and thus the utility of biological catalysts has been greatly limited. Attempts have been made to overcome this limitation by finding a way to artificially generate high-energy, nonphysiological and biological electron sources, including enzyme cofactor electron sources. Energy requiring enzymes such as formate dehydrogenase, hydrogenase, or ntrogenase could then be used in the synthesis of fuel or other important chemicals and in highly specific electrochemical sensors.

In order to catalyze a biochemical reaction involving one or more biochemical substrates, an enzyme must be capable of effecting electron transfer to or from the substrates. However, the amino acids which form the protein moieties of enzymes (the apoenzymes) cannot undergo changes in redox state. Therefore, all redox active enzymes require nonprotein, redox active organic, metal or metal-organic cofactors in order to perform these biological electron transfers. There exist several types of cofactors to accomplish a variety of electron transfer processes, each apoenzyme requiring a specific cofactor for activation.

In nature, electron transfer processes occur either between two protein-bound cofactors or between a protein bound cofactor and some small metabolic compound. Among the most versatile of the redox active cofactors are the flavin nucleotides which are involved both in transferring charge between protein-bound cofactors and in catalyzing metabolic redox changes. The flavin cofactors are unique because they can transfer either single or pairs of electrons. Flavin cofactors form an integral part of the redox active sites of many different enzymes. In these enzymes the apoenzyme confers specificity to the reaction, permitting only specific chemicals to arrive at the active site. Thus, a given cofactor can perform several different processes depending on the protein environment at a specific active site. These redox active flavin cofactors are derived from flavin compounds having the formula

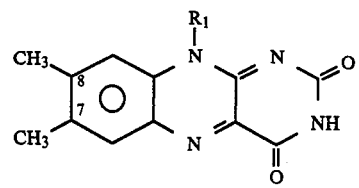

in which $R_1$ is a ribose derivative; e.g. riboflavin (RF), flavin mononucleotide (FMN) and flavin adenine dinucleotide (FAD). In natural systems FMN and FAD allow the required electron transfer between substrates.

Attempts have been made to provide electrochemical control of such biochemical reactions and regeneration of the flavin cofactor's redox state by coupling the natural system (e.g. the cofactor, apoenzyme and substrate) with an electronic assembly (e.g. an electrode and a current source). Many of these methods, however, have had the disadvantages of less than optimum electron transfer efficiency, diffusional resistance, chemical instability of the components, steric and electronic interference, and/or adherence problems.

As in designing any electrocatalytic system, a method must be found for rapidly and efficiently transporting charges between the electrocatalytic species (in this case the enzyme cofactor) and the electrode surface. Additionally, the biochemical substrate must be free to interact with the electrocatalytic species without steric or electronic interference. Thus, a need exists for a means of achieving a more direct electronic linkage between the electrode and the active site of the enzyme in order to effect efficient energy transfer for the catalysis of many biochemical reactions.

The orientation of the cofactor in the enzyme has been found to be critical for the proper functioning of the enzyme. For example, it is usually found that the flavin cofactors must be oriented with the benzenoid end of the flavin cofactor projecting into the solution, while the other, heterocyclic end is surrounded by the apoenzyme. Attempts have been made to avoid steric and electronic interference by coupling the flavin cofactor to the electrode surface at the flavin 8-alpha methyl position. However, prior to the present invention, most such electrodes have required strongly basic coupling conditions, have exhibited a low biological activity level, and have been subject to breakdown of the chemical bond at the 8-alpha methyl position of the flavin moiety when exposed to even weakly basic environments.

The successful formation of an efficient, biologically active, chemically stable, electrochemically coupled flavin cofactor modified electrode would provide the basis for the development of a new class of bioelectronic detectors and catalysts. Further, the use of an appropriate means of linking the electrode surface and the cofactor would allow large active surface coverages of the cofactor-mediators and encourage effective electron transfer from the electrode to the enzyme by presenting a low energy barrier to such transfer due to the short, low resistance distance (less than 10 angstroms) between the electrode and the enzyme. Monitoring the current flow from an electrode with a protein renatured on its surface or a flavoprotein or holoenzyme in solution would allow specific quantitation (due to enzymatic specificity) of analytes by convenient electronic methods. Further, using the electrode to maintain the biological cofactor at a specific potential would permit biocatalytic reactions to be driven by electrochemical energy without the need for replenishing of the expensive biological energy sources, e.g. redox active cofactors.

Commonly owned, copending U.S. application Ser. No. 862,951, filed May 14, 1986 and issued Nov. 3, 1987 as Pat. No. 4,744,193, disclosing a cofactor modified electrode in which a flavin cofactor moiety is bonded to an electrode surface via an imidazole moiety and a suitable linking group, presents to the art one such modified electrode, as well as methods for its preparation and use.

SUMMARY OF THE INVENTION

The present invention presents to the art other novel, stable and efficient cofactor modified electrodes and methods for electrochemically interfacing an enzyme to an electrode, overcoming the above-described limitations, as well as methods of preparing the novel electrodes.

The electrodes and methods of the present invention involve coupling biological and electronic processes to effect electron transfer between an electrode and one or more biochemical substrates by activating an enzyme selected to catalyze the reaction at a working surface of the electrode through a suitable redox active flavin cofactor bonded to the electrode.

A cofactor modified electrode, according to one aspect of the invention, comprises an electrode having a working surface of an electrically conducting or semiconducting material having an outer oxide or hydroxyl containing layer; and a redox active material electrochemically bonded to the outer layer of the electrode surface by means of a mercaptosilane derivative, preferably 3-mercaptopropyltriethoxysilane. The redox active material is derived from a redox active flavin compound being of formula I, wherein $R_1$ is a ribose derivative, preferably —$CH_2(CHOH)_3CH_2OH$, —$CH_2(CHOH)_3CH_2O$—$PO_3^{2-}$, —$CH_2(CHOCOCH_3)_3C$-$H_2OCOCH_3$, or

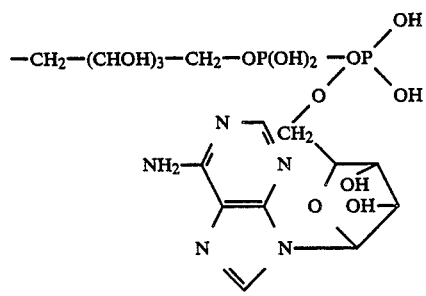

The flavin cofactor moiety is bonded to the sulfur atom of the mercaptosilane through the 8-alpha methyl position on the flavin structure. Thus, the redox active flavin cofactor moiety is oriented to permit coupling to a suitable apoenzyme in solution to form a renatured enzyme and to permit electron transfer between the electrode surface and the renatured enzyme, or to permit interaction with an enzyme in solution to permit electron transfer to activate the enzyme. The cofactor-to-electrode surface linkage is selected to allow the immobilized cofactor to retain its bioactivity.

A preferred cofactor modified electrode has a working surface of platinum, gold, silicon, InP, graphite, glassy carbon, tin dioxide, or a conducting polymer having an outer oxide or hydroxyl layer. Electrochemically bonded to the outer layer of a preferred electrode is a coating comprising groups of the formula

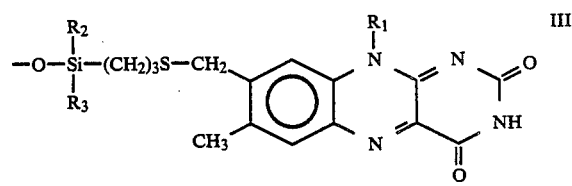

wherein $R_1$ is a ribose derivative as described above, and $R_2$ and $R_3$ are each independently an —O—$C_2H_5$ group, a hydroxyl group, or an —O— link to an adjacent silane group or to the outer layer of the electrode surface.

According to another aspect of the invention, a method of effecting electron transfer between an electrode having a working surface of an electrically conducting or semiconducting material and an enzyme comprises modifying the working surface of the electrode by electrochemically bonding a redox active material to an existing or derivatized outer oxide or hydroxyl layer on the working surface, by means of a mercaptosilane linking group. The redox active material is derived from a redox active flavin compound of formula I, in which the flavin compound is selected to activate the enzyme, i.e. $R_1$ is a ribose derivative chosen to provide the selected flavin cofactor moiety. The flavin cofactor moiety is bonded to the sulfur atom of the mercaptosilane through the 8-alpha methyl position on the flavin structure. The modified working surface of the electrode is immersed in an electroyte solution containing the enzyme or the protein moiety of the enzyme, and an electric potential is applied to the electrode sufficient to effect the electron transfer between the electrode surface and the enzyme through the redox active material.

A method of electrochemically mediating the catalysis of a reaction involving one or more biochemical substrates by an enzyme, according to another aspect of the invention, comprises modifying the working electrode as described for the above method, and establishing in an electrochemical cell, having at least the modified electrode and an auxiliary electrode, an electrolyte solution containing one or more biochemical substrates and an enzyme or the protein moiety of an enzyme suitable for catalyzing the reaction. An electric potential is applied to the electrodes sufficient to effect electron transfer between the electrode and the biochemical substrate through the redox active material and the enzyme.

According to yet another aspect of the invention, a method for coating an electrode substrate having a working surface of an electrically conducting or semiconducting material having an outer oxide or hydroxyl layer comprises electrochemically bonding a redox active material to the outer layer by means of a mercaptosilane linking group. The redox active material is derived from a redox active flavin compound of formula I, in which $R_1$ is as described above. The flavin derivative is bonded to the sulfur atom of the linking group through the 8-alpha methyl position on the flavin structure.

According to still another aspect of the invention, a method is presented for preparing a working electrode for electrochemically mediating the catalysis of a biochemical reaction by an enzyme. A working surface of the electrode, the working surface being of an electrically conducting or semiconducting material having an outer oxide or hydroxyl layer, is immersed in a solution containing a mercaptosilane compound from which a suitable linking group may be derived, for a sufficient time to electrochemically bond a sufficient quantity of a derivative of the mercaptosilane to the outer layer to support sufficient redox active material. The working surface is then immersed in a solution containing a redox active material derived from a flavin compound for a sufficient time to electrochemically bond sufficient redox active material to the outer layer of the working surface, by means of the linking group, to provide a working electrode capable of electrochemically mediating the catalysis of the biochemical reaction.

The flavin compound is of formula I, in which $R_1$ is a ribose derivative, preferably: $-CH_2(CHOH)_3CH_2OH$, $-CH_2(CHOH)_3CH_2O-PO_3^{2-}$, $-CH_2(CHOCOCH_3)_3CH_2OCOCH_3$, or formula II. The preferred linking group is derived from a silane compound of the formula

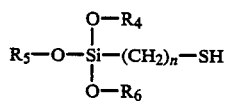

in which $R_4$, $R_5$ and $R_6$ are independently selected from the Si ligands displaceable by a hydroxide anion, and n is a positive integer from 1 to 20. The most preferred linking group is 3-mercaptopropyltriethoxysilane. The electrode is immersed in the solution for a sufficient time to electrochemically bond sufficient redox active material to the outer layer on the working surface, by means of the linking group, to provide a working electrode capable of electrochemically mediating the catalysis of the biochemical reaction. In one method, the reactions take place in an electrochemical cell containing an auxiliary electrode. An electrical potential is established across the electrodes during bond formation.

The bonding to the electrode surface of a site-specific derivative of the flavin cofactor, linked at the 8-alpha methyl position on the cofactor's structure, leaves the electron transport properties and bioactivity capabilities of the biological cofactor intact and, equally important, provides chemical stability to the modified electrode by protecting the flavin's 8-alpha methyl bond from chemical attack.

BRIEF DESCRIPTION OF THE DRAWING

For a better understanding of the present invention, together with other objects, advantages, and capabilities thereof, reference is made to the following disclosure and appended claims, together with the Drawing, in which:

DETAILED DESCRIPTION OF PREFERRED EMBODIMENTS

Figure 1:
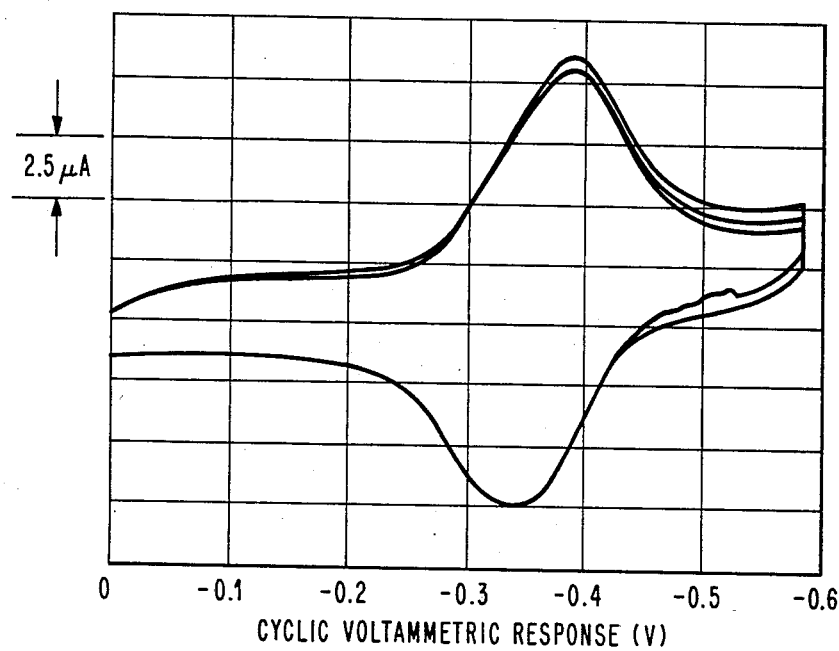
FIG. 1 is a tracing of a cyclic voltammetric response of a flavin electrode modified according to the invention.

A cofactor modified electrode according to the invention comprises a flavin cofactor moiety bonded to an electrically conducting or semiconducting working surface of an electrode by means of a mercaptosilane linking group. The linking group is preferably a derivative of $(CH_2H_5O)_3Si(CH_2)_3-SH$ (MPS). The working surface of the electrode is derivatized by known means to provide an outer oxide or hydroxyl layer to which the flavin derivative may be electrochemically coupled or bonded. The term "electrochemically coupled or bonded", as used herein, means that the bonding makes possible efficient electrochemical activity, i.e. rapid electron transfer, between the electrode surface and the mercaptosilane-flavin coating material, and may or may not include covalent bonding. Various electrode surface materials are possible, and are within the scope of this invention; for example, graphite or glassy carbon, platinum, gold, silicon, InP, tin dioxide or a conducting polymer.

The preferred flavin cofactor moiety is derived from a flavin compound having a ribose derivative moiety of the formula: $-CH_2(CHOH)_3CH_2OH$, $-CH_2(CHOH)_3CH_2O-PO_3^{2-}$, $-CH_2(CHOCOCH_3)_3C-H_2OCOCH_3$, or formula II. Thus the preferred flavin moiety is a derivative of a riboflavin (RF), flavin mononucleotide (FMN), tetraacetyl riboflavin (TARF), or flavin adenine dinucleotide (FAD), respectively. The flavin cofactor moiety is attached to the linking group through the 8-alpha methyl position of the flavin.

Using a mercaptosilane derivative as the bridge between the electrode surface and the bonded enzyme cofactor permits: (1) site-specific coupling of the flavin moiety to the electrode surface, (2) significantly retarded flavin decomposition due to milder surface derivatization conditions, (3) high concentration of the flavin cofactor on the electrode surface, and (4) rapid and efficient charge transfer between the electrode and the enzyme. Thus, the present invention achieves the benefits of both stable immobilization of the enzyme cofactor and rapid electron transfer.

Electrical activity may be observed if the cofactor moiety is sterically or electronically hindered; however, the orientation of the cofactor moiety on the coated electrode for effective coupling of the cofactor to the active site of the enzyme is critical to the efficient bioactivity of the modified electrode. The benzenoid end of the flavin cofactor is linked to the oxide or hyroxyl layer of the electrode working surface through the mercaptosilane linking group, freeing the heterocyclic end of the cofactor to be incorporated into or interact with the electroactive site of the enzyme. Rapid, efficient, and controlled electron transfer to or from the one or more biochemical substrates and regeneration of the cofactor's redox state are then effected by the electric potential applied to the electrode. Thus, a path for electron transfer is established between the electrode and the substrate(s) by way of the redox active coating.

The provision of a coating of a redox active material on an electrode surface, according to the invention, makes possible the method of this invention. A coated working electrode, for example a platinum electrode coated with the mercaptosilane-flavin redox active material described above, is introduced to an electrochemical cell containing an electrolyte solution including one or more biochemical substrates and a holoenzyme or apoenzyme capable of being activated by the cofactor moiety of the coated electrode and suitable for catalyzing a desired biochemical reaction involving the substrate(s). When an electric potential is applied to the working electrode, electron transfer takes place between the working surface of the electrode and the enzymatic cofactor bonded thereto. The direction in which the electron movement takes place depends on whether the working electrode is established as a cathode or as an anode.

The enzyme may be present in the solution as an apoenzyme, i.e. the protein moiety of the enzyme, or a holoenzyme, i.e. a complete enzyme, may be present in the solution or immobilized on the electrode surface. However, the enzyme must be capable of being activated by the cofactor moiety and be suitable for catalyzing the reaction.

The transfer of charge between the electrode and the cofactor is utilized to electrochemically generate the necessary form of the cofactor to activate the protein moiety of the enzyme in solution or renatured on the electrode working surface or, in the case of a holoenzyme in solution or immobilized on the electrode surface, to regenerate the redox state of the cofactor incorporated in the holoenzyme. The activated enzyme is then able to bind the secific biochemical substrate(s) to its active site, thus making possible the catalysis of the desired biochemical reaction involving the substrate(s).

For apoenzymes further requiring metal ions for activation, the appropriate metallic ions may be provided, if necessary, in the electrolyte solution within the electrochemical cell. The metallic ions in solution may be bound to the active site of the enzyme to complete activation of the enzyme.

The modified electrodes of the invention, the method of producing the electrodes and the use of such electrodes may be more completely understood by referring to the following Examples.

EXAMPLE 1

Preparation of the cofactor modified electrode:

All preparation procedures were performed under ambient conditions. The compound 8-alpha-bromo-O-tetraacetylriboflavin (BTF) was synthesized by the method described by Williamson et al. (*Biochem*, 24, p. 7790 (1985)). A freshly polished gold electrode was immersed in a solution of 20 mM of 3-mercaptopropyltriethoxysilane (MPS; available from Petrarch Systems, Inc., Bristol, Pa.) in methanol containing about 5 volume % water.

After 10 min, the electrode was removed from this solution and immediately immersed in a 2.0 mM solution of BTF in methanol for 1 hr at room temperature in the dark. After this flavin-coupling reaction, the electrode was dried for 24 hrs at room temperature in the dark, then rinsed extensively with ethanol prior to use. Characterization and testing of the modified electrode:

All electrochemical measurements were made in a single compartment electrochemical cell, under anaerobic ambient conditions, and using a platinum counter electrode and a standard calomel (SCE) reference electrode.

FIG. 1 illustrates the cyclic voltammetric response between 0 and $-0.6$ V in an aqueous buffered solution of pH 6.0 for the BTF cofactor modified electrode at a scan rate of 100 mV/sec, showing reversible electron transfer to and from the flavin cofactor moiety over many cycles. The flavin coverage on the working surface of the electrode, $2 \times 10^{-10}$ moles/cm$^2$, was calculated from the charge under the oxidation wave of FIG. 1 and the electrode surface area.

As expected for surface bound species, the magnitudes of the peak oxidation and reduction currents increased linearly with increasing scan rates from 5–500 mV/sec. At the 100 mV/sec scan rate illustrated in FIG. 1, the reduction and oxidation peak current separation was 40 mV; while the half-peak width of the anodic current is 120 mV, which is slightly larger than the theoretical value of 90.6 V (R. W. Murray, *Acc. Chem. Res.*, 13, p. 135 (1980)).

Similar voltammetric responses were obtained using platinum, tin dioxide, and glassy carbon electrode surfaces modified by procedures similar to that described above.

The coating formed was stable to several hundred voltammetric scans, to extensive rotating disk voltammetry, and to sonication in water, methanol, and acetonitrile. When stored in the absence of light, the electrode was stable for at least two weeks, and in many solvents (except strongly alkaline solutions).

Figure 2:
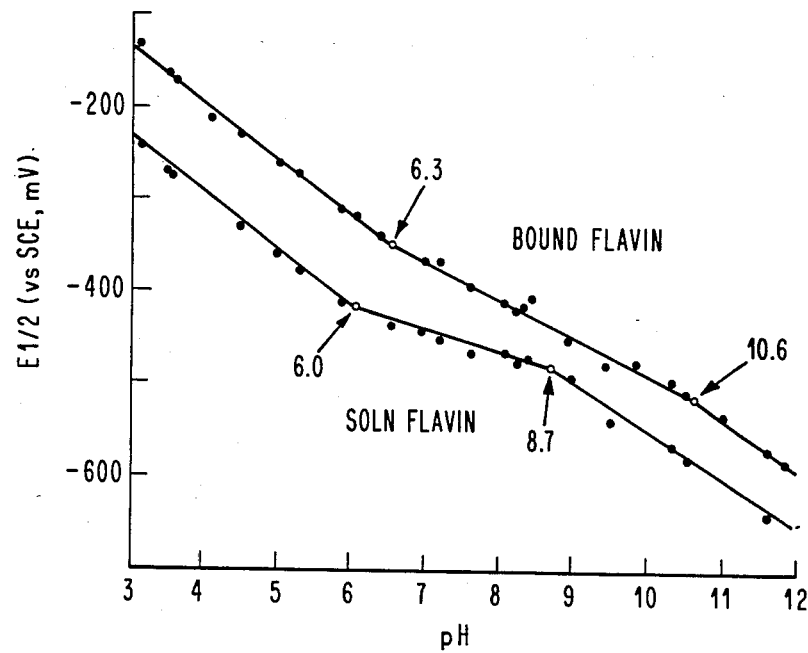
FIG. 2 is a plot of the variation of the half wave potential with pH for a flavin modified electrode according to the invention, and for the flavin in solution.

FIG. 2 plots the half wave potential at various pH values from 2.5–12 pH for a MPS-BTF coated platinum electrode, and for the flavin in solution. The close agreement between the profiles of the two curves strongly suggests that the bound electrochemically active flavin is to a great degree undecomposed. This Figure also shows that the MPS-BTF linkage is stable in an acidic solution.

EXAMPLE 2

An alternative method for preparing a cofactor modified electrode:

In an alternative method of preparing a flavin modified electrode, a flavin-mercaptosilane reagent was prepared reacting 2 mM BTF with 2 mM MPS in methanol-5% water solution for 10 min at room temperature in the dark. A freshly prepared gold electrode was placed in the solution for 30 min. The electrode was removed from solution and dried overnight at room temperature in the dark, then rinsed with ethanol prior to use.

Characterization and testing:

The modified electrode was characterized and tested as described above for the electrode of Example 1. Similar coverage was obtained, but the cyclic voltammograms indicated a less satisfactory response. Thus the electrode and method of Example 1 is preferred.

EXAMPLE 3

The BTF modified electrode, because of its stability in acidic solution, may be further derivatized by known methods to convert the surface bound BTF moiety to flavin mononucleotide (FMN) or flavin adenine dinucleotide (FAD) moieties. Thus, the BTF electrode may be modified to produce electrodes with FMN or FAD functionalities respectively.

Conversion of the surface bound BTF to flavin mononucleotide (FMN):

The BTF modified electrode of Example 1 is immersed in 0.1 M HCl in aqueous solution for 1 hr under ambient conditions to achieve deacetylation of the ribose group by acid hydrolysis. Subsequently, the electrode is immersed in 5 to 1 $POCl_3$/water (v/v) solution for 1.5 hr at 4° C. The $POCl_{13}$ solution is allowed to come to room temperature and the electrode allowed to remain immersed for 3.5 hr to form a surface bound FMN moiety by phosphorylation of the deacetylated ribose group. The MPS-FMN electrode is then rinsed with distilled water and allowed to stand in distilled water at room temperature for 24 hr.

EXAMPLE 4

Catalysis of the oxidation of lactate by means of the apoenzyme of lactate oxidase renatured on the electrode surface:

The above FMN modified electrode of Example 3 is then established as the working electrode in an electrolytic cell with a platinum auxiliary electrode and SCE reference electrode. The cell contains an anaerobic aqueous electrolyte solution of pH about 8.5, containing 0.5 M KCl, phosphate buffer, and the substrate lactate at 100 mM. A potential of +0.020 V relative to the SCE electrode is applied between the electrodes, the voltage being selected to be higher than the thermodynamic potential necessary to oxidize the lactate but lower than the potential needed by the electrode in the absence of the enzyme lactate oxidase. Little current flow is generated.

The apoenzyme of lactate oxidase is added to the electrolyte solution to give a concentration of about 1 nanomoles of active sites available for catalysis of the reaction. The current increases substantially with addition of the apoenzyme, demonstrating that the bound FMN cofactor is mediating the electron transfer from the modified electrode to lactate oxidase renatured on the surface of the electrode, therefore allowing it to oxidize lactate.

EXAMPLE 5

Catalysis of the oxidation of lactate by means of lactate oxidase holoenzyme in solution:

The procedure described in Example 4 is repeated, except that an equivalent amount of the holoenzyme of lactate oxidase replaces the apoenzyme in solution. Again, the current increases substantially with the addition of the holoenzyme. This increase in current demonstrates that the bound flavin is mediating the electron transfer from the modified electrode to the lactate oxidase enzyme in solution, therefore allowing it to mediate the oxidation of lactate.

EXAMPLE 6

Catalysis of the oxidation of lactate by means of lactate oxidase holoenzyme immobilized on the electrode surface:

The procedure of Example 5 is repeated, except that a small amount of the holoenzyme immobilized in known manner on the working surface of the MPS-FMN modified electrode replaces the holoenzyme added to the solution. The lactate oxidase is physically entrapped in an inert polyacrylamide gel and directly dispersed on the surface of a cellophane membrane having a pore size of 4–60 nm and a thickness of 0.127 mm. The membrane is secured to cover the modified working surface of the electrode, to provide physical contact between the flavin cofactor moiety of the electrode coating and the holoenzyme. The exact proportions of enzyme to gel are not critical, but the electrode assembly provides about $1 \times 10^{-10}$ moles/cm$^2$ of active sites. Yet again, the current increases substantially with the enzyme immobilized on the electrode as compared to the flavin modified electrode in electrolyte without the holoenzyme. This current increase demonstrates that the bound flavin is mediating the electron transfer from the electrode to the immobilized enzyme, allowing it to catalyze the oxidation of lactate in the electrolyte solution.

The cofactor modified electrodes according to the invention are capable of interacting with a wide variety of enzymes. The flavin cofactors display wide versatility in interacting with biological systems. Hundreds of proteins are known to require a flavin cofactor at their catalytic center for activation. Thus the modified electrodes according to the invention, having a flavin derivative bonded to the electrode working surface, can provide direct and efficient electronic linkages to many types of biological catalytic sites. The flavin modified electrodes of the invention may be utilized as "generic" devices whose specificity is determined by the specific enzyme used in a particular application. Such electrodes and the methods for their preparation and use are expected to provide the basis for development of highly useful bioelectronic detectors and catalyst systems.

While there has been shown and described what are at present considered the preferred embodiments of the invention, it will be obvious to those skilled in the art that various changes and modifications can be made therein without departing from the scope of the invention as defined by the appended claims.

What is claimed is:

1. A cofactor modified electrode comprising:
   an electrode substrate having a working surface of an electrically conducting or semiconducting material having an outer oxide or hydroxyl containing layer; ad
   a redox active material electrochemically bonded to the outer layer by means of a mercaptosilane linking group;
   wherein the redox active material is derived from a redox active flavin compound having the formula

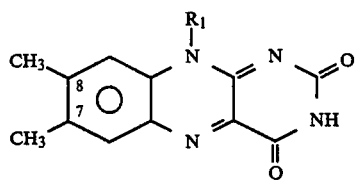

wherein $R_1$ is a ribose derivative, and the redox active material is bonded to the sulfur atom of the linking group through the 8-alphamethyl position on the redox active material.

2. An electrode according to claim 1 wherein the redox active material is criented to permit coupling of the redox active material to a suitable apoenzyme in a solution to form a renatured enzyme and to permit electron transfer between the electrode surface and the renatured enzyme.

3. A electrode according to claim 1 wherein the redox active material is oriented to permit electron transfer between the redox active material and a holoenzyme in a solution to activate the holoenzyme.

4. An electrode according to claim 1 wherein $R_1$ is selected from the group consisting of $-CH_2(CHOH)_3CH_2OH$, $-CH_2(CHOH)_3CH_2O-PO_3^{2-}$, $-CH_2(CHOCOCH_3)_3CH_2OCOCH_3$, and

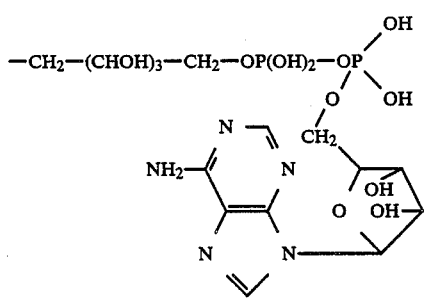

5. An electrode according to claim 1 wherein the working surface of the electrode is of a material selected from the group consisting of platinum, gold, tin dioxide, silicon, InP, graphite, glassy carbon, and conducting polymers.

6. An electrode according to claim 1 wherein the linking group is a derivative of a silane compound having the formula

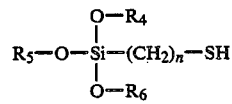

wherein $R_4$, $R_5$, and $R_6$ are independently selected from the Si ligands displaceable by a hydroxide anion, and n is a positive integer from 1 to 20.

7. A cofactor modified electrode comprising: an electrode substrate having a working surface of an electrically conducting or semiconducting material selected from the group consisting of platinum, gold, silicon, InP, graphite, glassy carbon, tin dioxide, and conducting polymers, the working surface having an outer oxide or hydroxyl layer; and
   a redox active coating electrochemically bonded to the outer layer and comprising groups of the formula

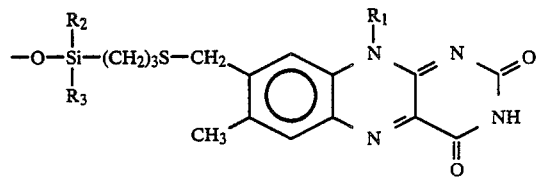

wherein $R_1$ is a ribose derivative selected from the group consisting of $-CH_2(CHOH)_3-CH_2OH$, $-CH_2(CHOH)_3CH_2O-PO_3^{2-}$, $-CH_2(CHOCOCH_3)_3CH_2OCOCH_3$, and $-CH_2(CHOH)_3CH_2O-P-O-P-O-CH_2$

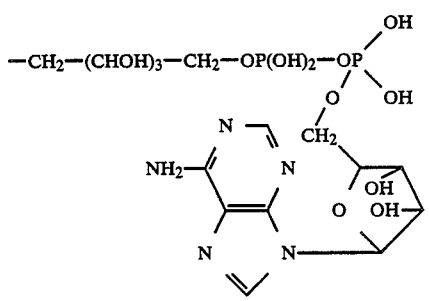

and $R_2$ and $R_3$ are each an $-O-C_2H_5$ group or an $-O-$ link to an adjacent silane group or to the outer layer of the electrode working surface, and may be the same or different.

8. A method of effecting electron transfer between an electrode having a working surface of an electrically conducting or semiconducting material and an enzyme comprising the steps of:
   modifying the working surface of the electrode by electrochemically bonding to an existing or derivatized outer oxide or hydroxyl layer on the working surface, by means of a mercaptosilane linking group, a redox active material derived from a redox active flavin -compound having the formula

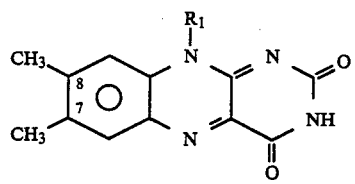

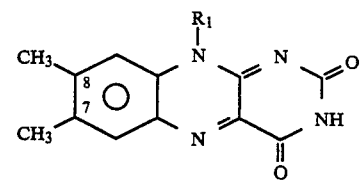

wherein the redox active material is selected to activate a protein moiety of the enzyme, $R_1$ being a ribose derivative selected to provide the selected redox active material, and the redox active material is bonded to the sulfur atom of the linking group through the 8-alpha methyl position on the redox active material;

immersing the modified working surface of the electrode in an electrolyte solution containing the protein moiety of the enzyme; and applying an electric potential to the electrode sufficient to effect the electron transfer between the electrode surface and the enzyme through the redox active material.

9. A method according to claim 8 wherein $R_1$ is selected from the group consisting of $-CH_2(CHOH)_3-CH_2OH$, $-CH_2(CHOH)_3CH_2O-PO_3{}^{2-}$, $-CH_2(CHOCOCH_3)_3CH_2OCOCH_3$, and

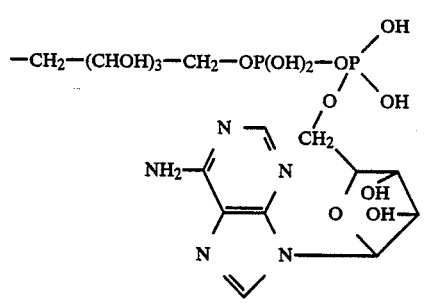

the working surface of the electrode is of a material selected from the group consisting of platinum, gold, tin dioxide, silicon, InP, graphite, glassy carbon, and conducting polymers, and the linking group is a derivative of a silane compound having the formula

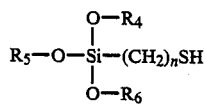

wherein $R_4$, $R_5$ and $R_6$ are independently selected from the Si ligands displaceable by a hydroxide anion, and n is a positive integer from 1 to 20.

10. A method of effecting electron transfer between an electrode having a working surface of an electrically conducting or semiconducting material and an enzyme comprising the steps of:

modifying the working surface of the electrode by electrochemically bonding to an existing or derivatized outer oxide or hydroxyl layer on the working surface, by means of a mercaptosilane linking group a redox active material derived from a redox active flavin compound having the formula wherein the redox active material is selected to activate the enzyme, $R_1$ being a ribose derivative selected to provide the selected redox active material, and the redox active material is bonded to the sulfur atom of the linking group through the 8-alpha methyl position on the redox active material immersing the modified working surface of the electrode in an electrolyte solution in an electrochemical cell;

introducing the enzyme to the electrochemical cell; and applying an electric potential to the electrode sufficient to effect the electron transfer between the electrode surface and the enzyme through the redox active material.

11. A method according to claim 10 wherein the step of introducing the enzyme to the electrochemical cell comprises adding the enzyme to the electrolyte solution.

12. A method according to claim 10 wherein the step of introducing the enzyme to the electrochemical cell comprises immobilizing the enzyme on the working surface of the electrode.

13. A method according to claim 10 wherein $R_1$ is selected from the group consisting of $-CH_2(CHOH)_3-CH_2OH$, $-CH_2(CHOH)_3CH_2O-PO_3{}^{2-}$, $-CH_2(CHOCOCH_3)_3CH_2OCOCH_3$, and

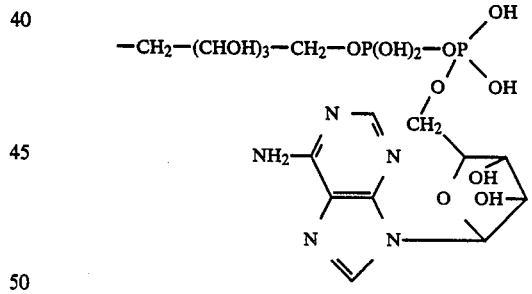

the working surface of the electrode is of a material selected from the group consisting of platinum, gold, tin dioxide, silicon, InP, graphite, glassy carbon, and conducting polymers, and the linking group is a derivative of a silane compound having the formula

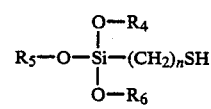

wherein $R_4$, $R_5$ and $R_6$ are independently selected from the Si ligands displaceable by a hydroxide anion, and n is a positive integer from 1 to 20.

14. A method of electrochemically mediating the catalysis of a reaction involving one or more biochemical substrates by an enzyme comprising the steps of: modifying a working surface of a working electrode by electrochemically bonding to an existing or derivatized oxide or hydroxyl layer on the working surface, by means of a mercaptosilane linking group, a redox active material derived from a redox active flavin compound having the formula

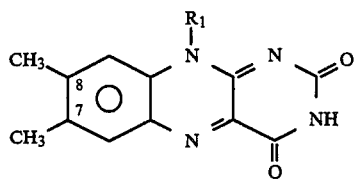

wherein the redox active material is selected H to activate a protein moiety of the enzyme, $R_1$ being a ribose derivative selected to provide the selected redox active material, and the redox active material is bonded to the sulfur atom of the linking group through the 8-alpha methyl position on the redox active material;

establishing in an electrochemical cell having at least the modified electrode and an auxiliary electrode, an electrolyte solution containing the biochemical substrate(s) and the protein moiety of the enzyme suitable for catalyzing the reaction; and applying an electric potential to the electrodes sufficient to effect electron transfer between the modified electrode and the biochemical substrate through the redox active material and the enzyme.

15. A method according to claim 14 wherein the enzyme is a metalloenzyme and the electrolyte solution further contains one or more metallic ions suitable for coupling with the protein moiety and the redox active material to complete the enzyme.

16. A method according to claim 14 wherein $R_1$ is selected from the group consisting of —$CH_2(CHOH)_3$—$CH_2OH$, —$CH_2(CHOH)_3CH_2O$—$PO_3^{2-}$, —$CH_2(CHOCOCH_3)_3CH_2OCOCH_3$, and

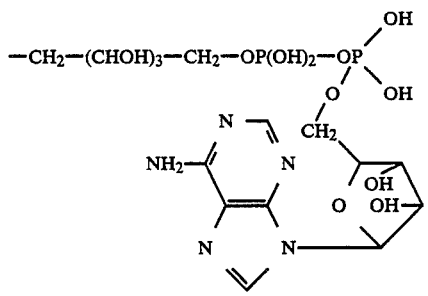

the working surface of the electrode is of a material selected from the group consisting of platinum, gold, tin dioxide, silicon, InP, graphite, glassy carbon, and conducting polymers, and the linking group is a derivative of a silane compound having the formula

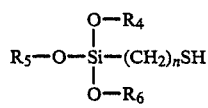

wherein $R_4$, $R_5$ and $R_6$ are independently selected from the Si ligands displaceable by a hydroxide anion, and n is a positive integer from 1 to 20.

17. A method of electrochemically mediating the catalysis of a reaction involving one or more biochemical substrates by an enzyme comprising the steps of:
modifying a working surface of an electrode by electrochemically bonding to an existing or derivatized outer oxide or hydroxyl layer on the working surface by means of a mercaptosilane linking group, a redox active material derived from a redox active flavin compound having the formula

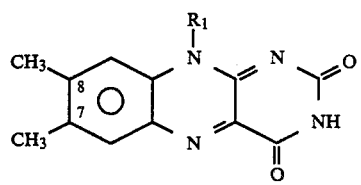

wherein the redox active ,aterial is selected to activate the enzyme, $R_1$ being a ribose derivative selected to provide the selected redox active material, and the redox active material is bonded to the sulfur atom of the linking group through the 8-alpha methyl position on the redox active material;

establishing in an electrochemical cell having at least the modified electrode and an auxiliary electrode an electrolyte solution containing the biochemical substrate(s)

introducing to the electrochemical cell the enzyme suitable for catalyzing the reaction; and applying an electric potential to the electrodes sufficient to effect electron transfer between the modified electrode and the biochemical substrate through the redox active material and the enzyme.

18. A method according to claim 17 wherein the step of introducing the enzyme to the electrochemical cell comprises adding the enzyme to the electrolyte solution.

19. A method according to claim 17 wherein the step of introducing the enzyme to the electrochemical cell comprises immobilizing the enzyme on the working surface of the electrode.

20. A method according to claim 17 wherein $R_1$ is selected from the group consisting of —$CH_2(CHOH)_3$—$CH_2OH$, —$CH_2(CHOH)_3CH_2O$—$PO_3^{2-}$, —$CH_2(CHOCOCH_3)_3CH_2OCOCH_3$, and

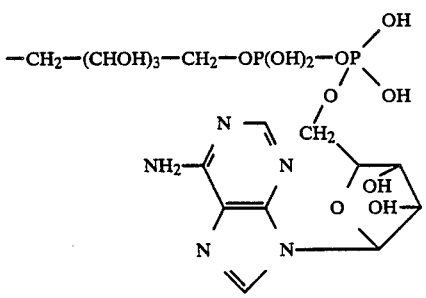

the working surface of the electrode is of a material selected from the group consisting of platinum, gold, tin dioxide, silicon, InP, graphite, glassy carbon, and conducting polymers, and the linking group is a derivative of a silane compound having the formula

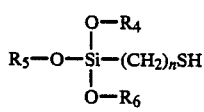

wherein $R_4$, $R_5$ and $R_6$ are independently selected from the Si ligands displaceable by a hydroxide anion, and n is a positive integer from 1 to 20.

21. A method for coating an electrode substrate having a working surface of an electrically conductive or semiconductive material having an outer oxide or hydroxyl layer comprising:
   electrochemically bonding a redox active material to the outer layer by means of a mercaptosilane linking group;
   wherein the redox active material is derived from a redox active flavin compound having the formula

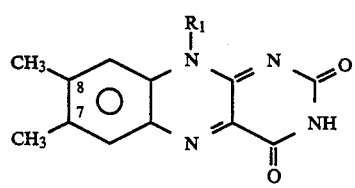

wherein $R_1$ is a ribose derivative, and the redox active material is bonded to the sulfur atom of the linking group through the 8-alpha methyl position on the redox active material.

22. A method according to claim 21 wherein $R_1$ is selected from the group consisting of $-CH_2(CHOH)_3-CH_2OH$, $-CH_2(CHOH)_3CH_2O-PO_3^{2-}$, $-CH_2(-CHOCOCH_3)_3CH_2OCOCH_3$, and

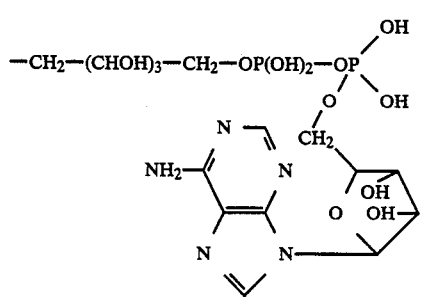

23. A method of preparing a working electrode for electrochemically mediating the catalysis of a biochemical reaction by an enzyme comprising the steps of:
   immersing a working surface of the electrode, the working surface being of an electrically conducting or semiconducting material having an outer oxide layer on the working surface, in a solution containing a mercaptosilane compound from which a suitable linking group may be derived, for a sufficient time to electrochemically bond a sufficient quantity of a derivative of the mercaptosilane to the outer oxide layer to support sufficient redox active material;
   immersing the mercaptosilane derivatized working surface in a solution containing a redox active material derived from a redox active flavin compound having the formula

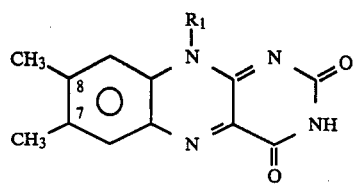

wherein $R_1$ is a ribose derivative, for a sufficient time to electrochemically bond sufficient redox active material to the outer oxide layer by means of the linking group to provide a working electrode caable of electrochemically mediating the catalysis of the biochemical reaction.

24. A method according to claim 23 wherein the working surface of the electrode is of a material selected from the group consisting of platinum, gold, tin dioxide, silicon, InP, graphite, glassy carbon and conducting polymers; the ribose derivative is selected from the group consisting of $-CH_2(CHOH)_3-CH_2OH$, $-CH_2(CHOH)_3CH_2O-PO_3^{2-}$, $-CH_2(-CHOCOCH_3)_3CH_2OCOCH_3$, and

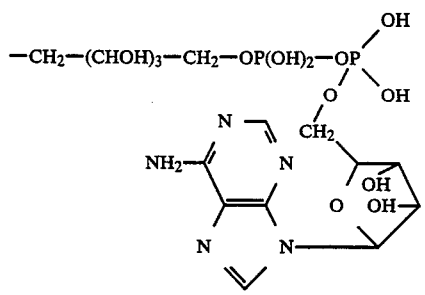

and the compound from which a suitable linking group may be derived is a silane compound having the formula

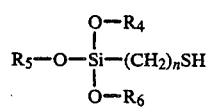

wherein $R_4$, $R_5$, and $R_6$ are independently selected from the group consisting of Si ligands displaceable by a hydroxide anion, and n is a positive integer from 1 to 20.

25. A method according to claim 23 wherein the immersing steps take place in an electrochemical cell containing an auxiliary electrode, and further comprising the step of establishing an electrical potential across the electrodes during bond formation of sufficient density and for sufficient time to electrochemically bond sufficient linking groups and redox active material to the outer layer to provide a working electrode capable of electrochemically mediating the catalysis of the biochemical reaction.

* * * * *